(12) United States Patent
Zhang

(10) Patent No.: US 10,278,595 B2
(45) Date of Patent: May 7, 2019

(54) ANALYSIS AND CHARACTERIZATION OF PATIENT SIGNALS

(71) Applicant: Siemens Medical Solutions USA, Inc., Malvern, PA (US)

(72) Inventor: Hongxuan Zhang, Palatine, IL (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/806,043

(22) Filed: Nov. 7, 2017

(65) Prior Publication Data

US 2018/0064354 A1 Mar. 8, 2018

Related U.S. Application Data

(62) Division of application No. 14/514,631, filed on Oct. 15, 2014, now Pat. No. 9,848,785.

(60) Provisional application No. 61/912,217, filed on Dec. 5, 2013.

(51) Int. Cl.
| | | |
|---|---|---|
| *A61B 5/1455* | (2006.01) | |
| *A61B 5/024* | (2006.01) | |
| *A61B 5/00* | (2006.01) | |
| *A61B 5/026* | (2006.01) | |

(52) U.S. Cl.
CPC .......... *A61B 5/02438* (2013.01); *A61B 5/026* (2013.01); *A61B 5/14551* (2013.01); *A61B 5/7246* (2013.01); *A61B 5/7282* (2013.01)

(58) Field of Classification Search
None
See application file for complete search history.

(56) References Cited

U.S. PATENT DOCUMENTS

| | | |
|---|---|---|
| 5,113,861 A | 5/1992 | Rother |
| 6,485,429 B2 | 11/2002 | Forstner |
| 6,961,600 B2 | 11/2005 | Kohl et al. |
| 6,987,994 B1 | 1/2006 | Mortz |
| 7,008,380 B1 | 3/2006 | Rees et al. |
| 7,330,750 B2 | 2/2008 | Erkkila et al. |
| 7,367,949 B2 | 5/2008 | Korhonen et al. |
| 7,794,406 B2 | 9/2010 | Reisfeld et al. |
| 7,806,832 B2 | 10/2010 | Gallagher et al. |
| 2001/0039383 A1 | 11/2001 | Mohler |
| 2002/0082507 A1 | 6/2002 | Kolluri et al. |
| 2004/0171948 A1 | 9/2004 | Terry |
| 2004/0267324 A1 | 12/2004 | Geheb et al. |
| 2006/0149144 A1 | 7/2006 | Lynn et al. |
| 2007/0191697 A1 | 8/2007 | Lynn et al. |
| 2007/0255146 A1 | 11/2007 | Andrews et al. |
| 2008/0066753 A1 | 3/2008 | Martin et al. |
| 2008/0269832 A1 | 10/2008 | Wong et al. |
| 2009/0131774 A1 | 5/2009 | Sweitzer et al. |
| 2009/0253968 A1 | 10/2009 | Cho et al. |
| 2009/0318787 A1 | 12/2009 | Aoyagi et al. |
| 2010/0191074 A1 | 7/2010 | Chou |

(Continued)

*Primary Examiner* — Eric F Winakur
*Assistant Examiner* — Marjan Fardanesh

(57) ABSTRACT

Disclosed herein is a framework for facilitating patient signal analysis. In accordance with one aspect, first and second patient signal data are received from a patient monitor. The first and second patient signal data may then be segmented into respective first and second regions of interest, from which respective first and second waveform parameters may be extracted. One or more morphology indices may then be generated based on the first and second waveform parameters to compare shapes of the first and second regions of interest.

19 Claims, 9 Drawing Sheets

(56) References Cited

U.S. PATENT DOCUMENTS

2010/0234705 A1 9/2010 Lynn et al.
2012/0150003 A1 6/2012 Zhang
2012/0179382 A1 7/2012 Zhang

| | Normal arm artery | Low flexibility arm artery |
|---|---|---|
| Blood pressure measurement (Systolic/Diastolic) | 122/83 mmHg | 126/84 mmHg |
| SPO2 oximetric saturation percentage value | 99% | 99% |
| BMTV $\dfrac{Variability(T_{PB1}-T_{PB3})}{5}$ $\dfrac{Variability(T_{PS1}-T_{PS3})}{5}$ | 2.8 | 13.6 |

ANALYSIS AND CHARACTERIZATION OF PATIENT SIGNALS

CROSS-REFERENCE TO RELATED APPLICATION

This is a divisional application which claims the benefit of U.S. non-provisional application Ser. No. 14/514,631 filed on Oct. 15, 2014, which claims the benefit of provisional application No. 61/912,217 filed on Dec. 5, 2013, the entire contents of which are incorporated herein by reference.

TECHNICAL FIELD

The present disclosure generally relates to systems and methods for analyzing and characterizing patient signals.

BACKGROUND

Blood vessels, particularly those within the artery vessel system, provides nutrition and oxygen to every part of the body and therefore plays a significant role in protecting the health of the body. Pathologies within the blood circulation system may cause a patient's hemodynamic status to change rapidly. By monitoring and diagnosing blood vessel functionality, on-time detection of pathologies and abnormalities within the blood circulation system will be greatly enhanced. Peripheral capillary oxygen saturation (SPO2) and blood pressure measurements are typical clinical approaches to measure and capture blood flow and oximetric parameters. However, blood pressure waveform and SPO2 waveforms, which come from the same source (i.e., heart), have not been untied and combined to monitor the blood circulation system. There are no known quantitative and qualitative methods that use both blood pressure and SPO2 signals to quantify and characterize vessel health status efficiently and effectively. Furthermore, blood pressure waveform and SPO2 waveform and data diagnosis require extensive experience and clinical knowledge that may delay clinical workflow, treatment and drug delivery, which may increase clinical risk and hazards to the patients.

Traditional clinical diagnosis and evaluation methods typically focus on parameter deviations and changes of the waveform data, such as SPO2 oxygen saturation level, R wave amplitude, RR wave interval and duration, ST segment voltage, etc. However, if the amplitude and timing of these parameters are not changing, clinical users may easily ignore or pay less attention to tiny and subtle changes in waveform morphology.

Currently, there are no known methods that efficiently and effectively combine and analyze both oximetric and blood pressure waveforms and data. Additionally, conventional clinical methods include some mapping technologies, such as intra-cardiac electrograms (ICEG) mapping of the three-dimensional (3D) heart function. However, there are no known efficient mapping methods for multi-channel blood pressure and SPO2 signals for heart or whole circulation system. Further, known clinical SPO2-based methods focus on the oxygen content in the blood, which may help to monitor functions of the lung, heart and respiration. However, these techniques are typically qualitative, and may not be able provide precise information on the severity, type, location, trend, etc., of the pathology. Even further, most conventional catheter technologies and Implantable Cardioverter-Defibrillator (ICD) devices use intra-cardiac electrograms or electrophysiological action potential signals to diagnose and control the pacing rate and electrical shock treatment (e.g., cardiac ablation to eliminate fibrillation). Blood and SPO2 signals are not known to be used in a closed loop treatment.

Accordingly, there exists a need to provide an improved framework to address these deficiencies and related problems.

SUMMARY

The present disclosure relates to a framework for facilitating patient signal analysis. In accordance with one aspect, first and second patient signal data are received from a patient monitor. The first and second patient signal data may then be segmented into respective first and second regions of interest, from which respective first and second waveform parameters may be extracted. One or more morphology indices may then be generated based on the first and second waveform parameters to compare shapes of the first and second regions of interest.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
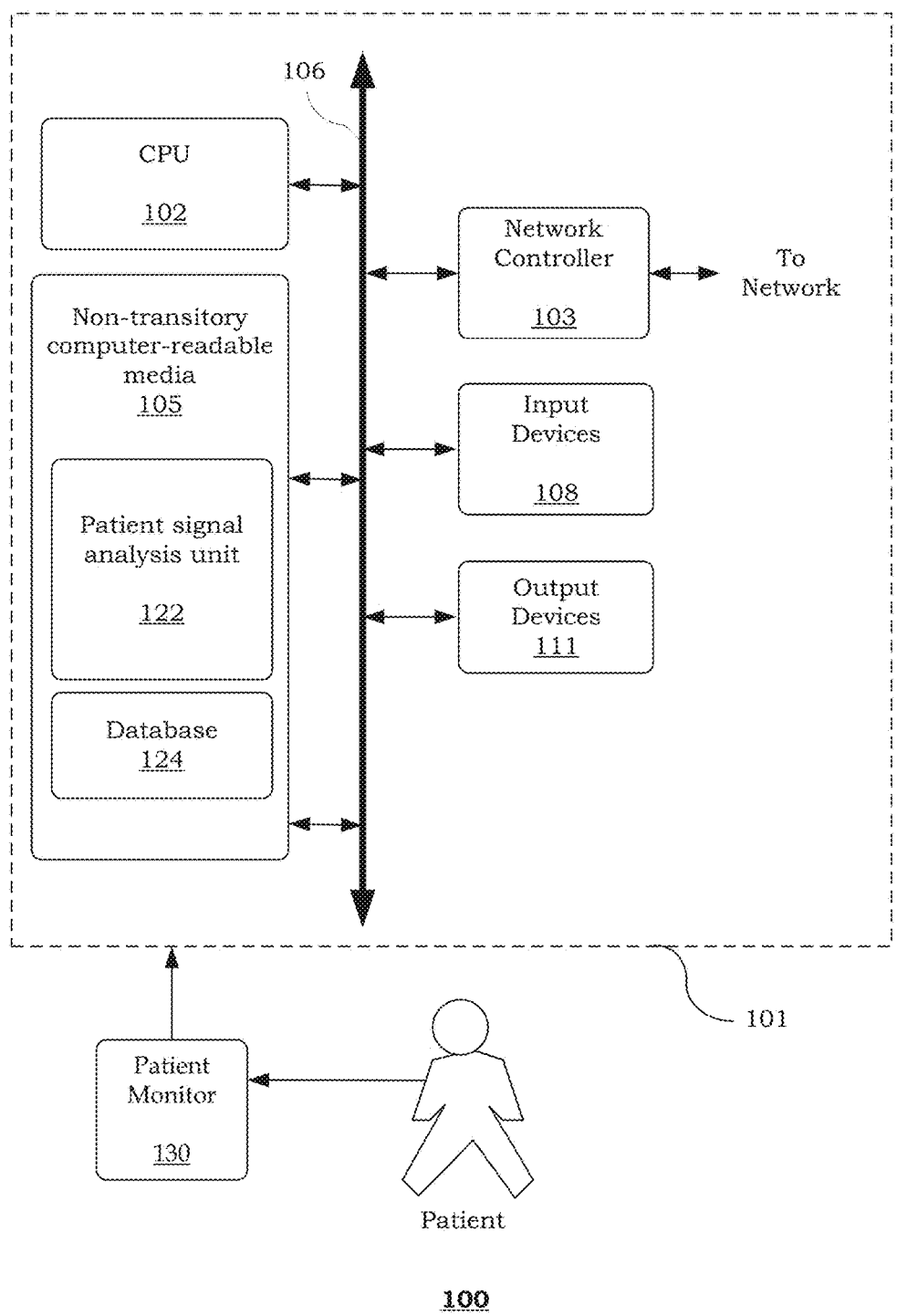
FIG. 1 shows an exemplary system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the system and methods described herein may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

It is to be further understood that since the constituent system modules and method steps depicted in the accompanying Figures are preferably implemented in software, the actual connections between the system components (or the flow of the process steps) may differ depending upon the manner in which the present invention is programmed. Given the teachings herein, one of ordinary skill in the related art will be able to contemplate these and similar implementations or configurations of the present invention.

The present framework provides a methodology to combine and analyze patient signals. In accordance with some implementations, the framework combines multi-channel blood pressure and oximetric signals, and monitors the signal waveforms to detect pathologies and tissue malfunctions in, for example, the cardiac chambers, body or brain artery blood flow system. A set of quantitative and qualitative parameters (e.g., morphology ratios and indices) may be derived to sensitively and specifically detect and characterize blood pressure versus oxygen transition modes and patterns in the circulation system, such as timing, speed, and volume from lung to heart, and to capillary arteries. The parameters may be used to quantify, evaluate and/or map malfunctions, abnormalities and/or pathologies (e.g., type, severity, trend, location, etc.) in a blood circulation system, such as the cardiac vascular system, body arterial system, brain vessel blood flow system, etc.

The present framework advantageously improves the precision and reliability of patient signal analysis and interpretation of circulation system health status and activities. The technologies in the present framework may be used to, for example, identify blood circulation disorders, differentiate cardiac arrhythmias, characterize vessel pathological severities, predict life-threatening events, or evaluate drug delivery and effects. These and other features, applications and advantages will be described in more details herein.

For purposes of illustration, the present framework is described herein in the context of blood pressure and oximetric signals. However, it should be appreciated that the present framework is also useful for analyzing other types of electrophysiological signals, including but not limited to, cardiac sound, respiration, blood flow oscillation, electrocardiography (ECG), electroencephalography (EEG) or magnetoencephalography (MEG) signals.

FIG. 1 shows an exemplary system 100 for implementing a method and system of the present disclosure. It is to be understood that, because some of the constituent system components and method steps depicted in the accompanying figures can be implemented in software, the actual connections between the systems components (or the process steps) may differ depending upon the manner in which the present framework is programmed. For example, the system 100 may be implemented in a client-server, peer-to-peer (P2P) or master/slave configuration. In such configurations, the system 100 may be communicatively coupled to other systems or components via a network, such as an Intranet, a local area network (LAN), a wide area network (WAN), a P2P network, a global computer network (e.g., Internet), a wireless communications network, or any combination thereof. Given the teachings of the present framework provided herein, one of ordinary skill in the related art will be able to contemplate these and similar implementations or configurations.

As shown in FIG. 1, the system 100 includes a computer system 101 and a patient monitor 130. The computer system 101 may include, inter alia, a central processing unit (CPU) 102, a non-transitory computer-readable media 105, one or more output devices 111 (e.g., printer, display monitor, projector, speaker, etc.), a network controller 103, an internal bus 106 and one or more input devices 108 such as, for example, a keyboard, mouse, touch screen, gesture and/or voice recognition module, etc. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein may be implemented as computer-readable program code tangibly embodied in non-transitory computer-readable media 105. Non-transitory computer-readable media 105 may include random access memory (RAM), read only memory (ROM), magnetic floppy disk, flash memory, and other types of memories, or a combination thereof. The present techniques may be implemented by patient signal analysis unit 122 that is stored in computer-readable media 105. As such, the computer system 101 is a general-purpose computer system that becomes a specific purpose computer system when executing the computer-readable program code.

The same or different computer-readable media 105 may be used for storing a database 124. Database 124 may include a repository of determined parameters and ratios, selectable predetermined functions, patient signal data, (e.g., electrophysiological, SPO2, respiration signal data, etc.), patient data (e.g., demographic data, pathology history, etc.), other input data and/or other derived output parameters. Patient signal data may be provided by a patient monitor 130 that is communicatively coupled to the computer system 101.

Patient monitor 130 may be used to acquire various types of patient biometric or physiological signal information for monitoring the patient. For example, the monitoring information may include, but is not limited to, electrophysiological signal data (e.g., ECG, ICEG, etc.), oximetric or SPO2 signal data, respiration signal data, blood pressure, temperature and/or other patient biometric, physiological or medical parameter information. The patient monitor 130 may include appropriate biometric sensors (e.g., leads for surface ECG and catheter for intra-cardiac electrograms) for acquiring the monitoring patient signals. Implementations of the present framework provide parameters to detect, diagnose and quantify such patient signals.

Figure 2:
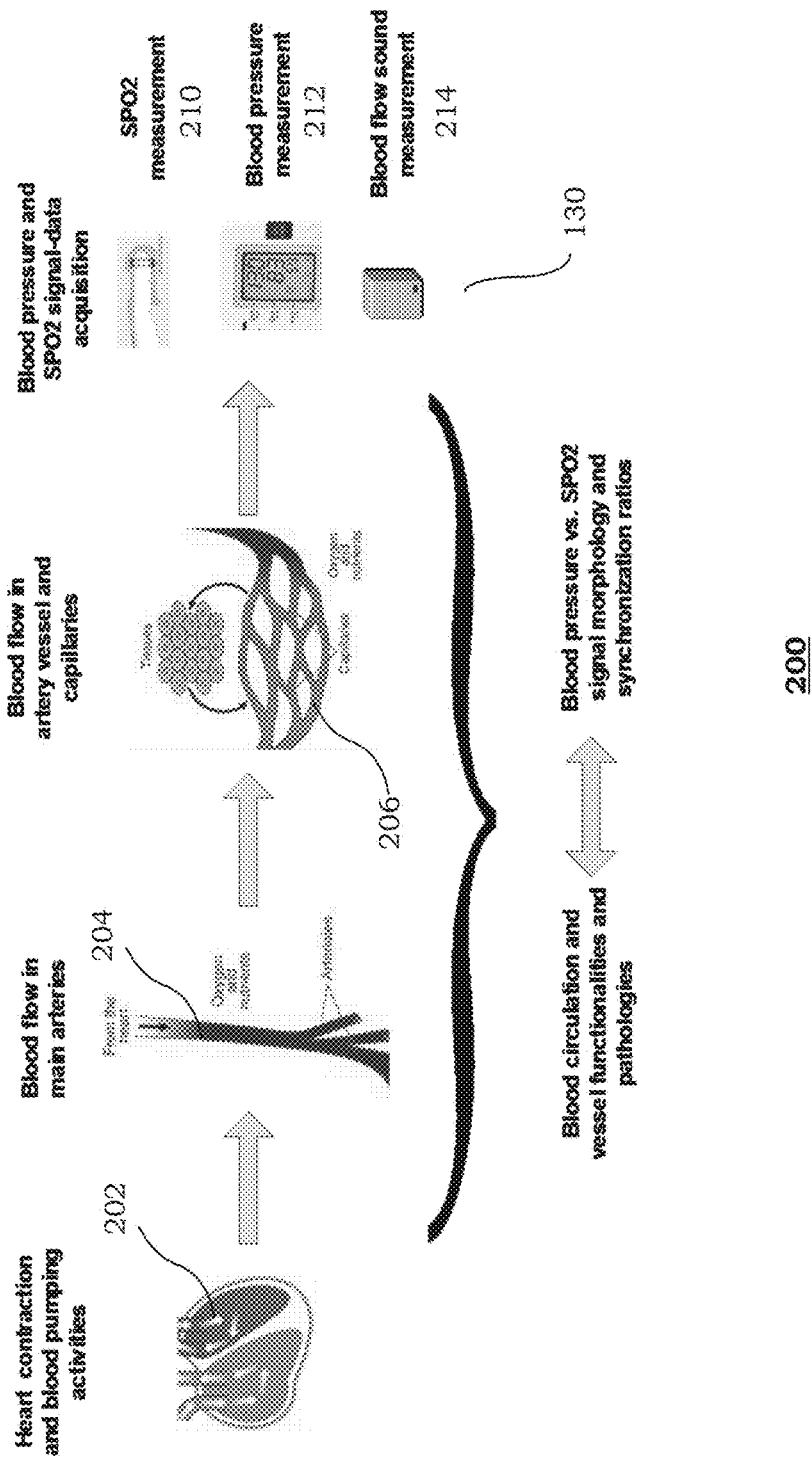
FIG. 2 is a schematic diagram that illustrates the mapping of blood flow.

In accordance with some implementations, patient monitor 130 includes a multi-channel patient signal measurement system operable to simultaneously acquire different types of signal data from the patient, such as blood pressure data, blood flow sound data and oximetric data. FIG. 2 is a schematic diagram that illustrates the mapping of blood flow from the heart to the vessels and capillaries where the blood pressure, blood flow and oximetric level may be simultaneously measured by a multi-channel blood sensor and data acquisition system. Typically, blood with oxygen flows to the left ventricle of the heart 202, and is pumped out by ventricular chambers to the main artery 204, which transports the oxygenated blood to many parts of the body. For example, blood flows from vessels and capillaries to organ tissues, from big vessels to small vessels, then finally to capillaries 206. Hence, blood pressure, blood flow and oximetric waveforms can reflect dynamic characteristics of cardiac functions and blood vessels, such as contracting strength, energy, duration, syncing timing, etc. Oximetric (e.g., SPO2) level 210, blood pressure 212 and blood flow 214 may be measured non-invasively by multi-channel blood sensor and data acquisition system 130. In some implementations, multi-channel blood sensor and data acquisition system 130 includes a pressure force sensor (or mechanical/electrical sensors) and light sensor to be placed on or near the blood vessel (e.g., artery vessel branch, capillaries, etc.). The blood vessel may be located in, for example, the arm, leg or fingertip of the patient. Theoretically, a bridge or link can be built between blood flow and blood circulation function and activities. One aspect of the present framework monitors, diagnoses, and/or characterizes blood flow circulation and blood vessel functions by using a combination of blood pressure and oximetric signal waveform morphologies and related parameters. In order to combine and compare the blood flow information (e.g., blood pressure waveform, blood flow oscillation sound, etc.) and blood content information (e.g., oxygen ratio, saturation, etc.), new designs and methods to acquire the said waveforms and data are needed.

Figure 3:
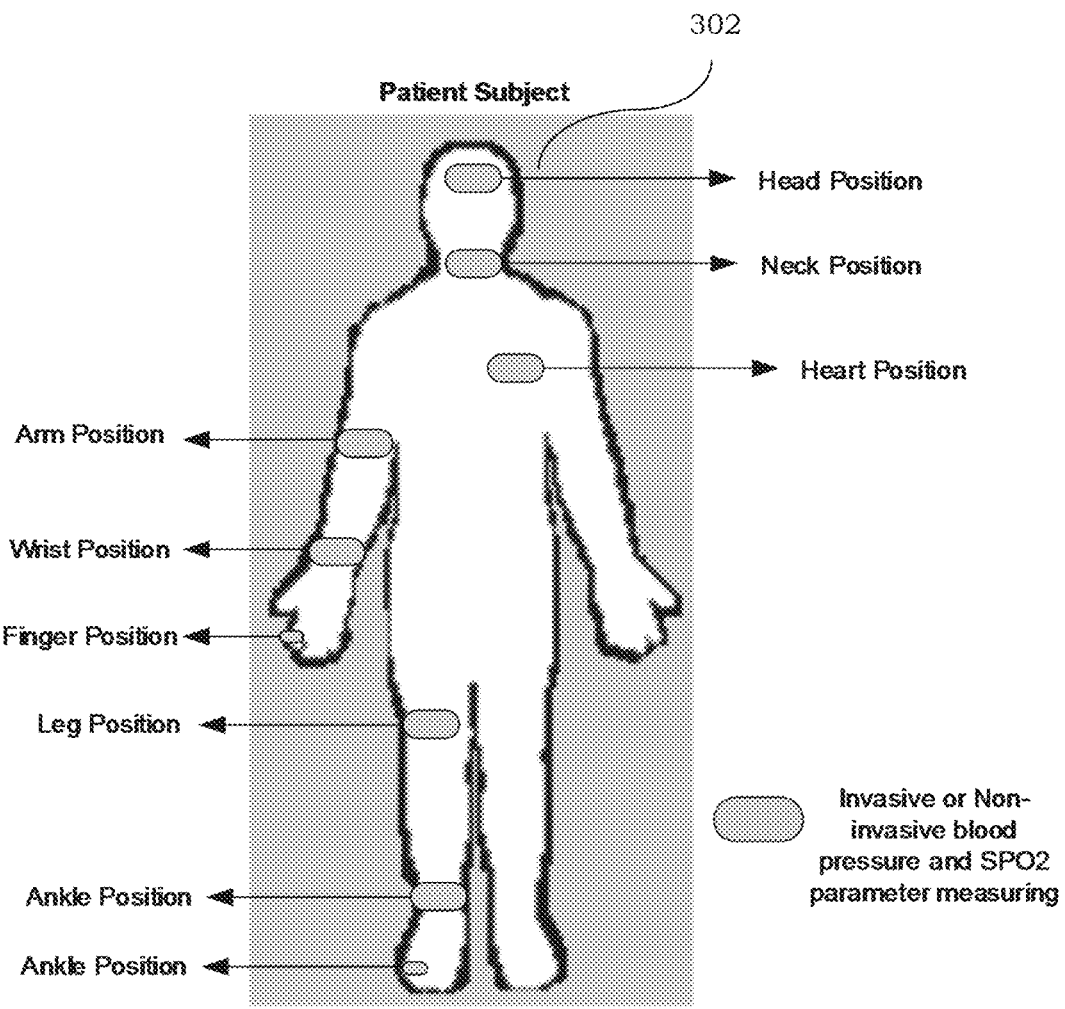
FIG. 3 illustrates exemplary positions of multi-channel blood sensors on a patient's body.

FIG. 3 illustrates exemplary positions of multi-channel blood sensors on a patient's body 302. Multiple sensors may be placed at different positions of the body 302 for invasive or non-invasive strategies of sensing, acquiring and analyzing patient signals (e.g., hemodynamic and blood pressure signals, oximetric signals, vital sign signals, etc.). According to the different positions, different kinds of testing signals for patient subject data sensing and acquisition may be utilized. For example, for the heart position (e.g., near heart chamber, coronary arteries, etc.), ultrasound and electromagnetic field sensors may be used. Laser sensors may be utilized in signal acquisition and monitoring for the finger position. As for the wrist, arm, finger and ankle positions, different kinds of methods and sensors may be selected based on measuring convenience, blood pressure, blood flow sound, oxygen content and its variation/changes. Ultrasound, laser, vibration-oscillation sensing-based hemodynamic and oximetric signal monitoring, etc., may be used. Recent clinical technological innovations have made it possible to non-invasively or invasively measure blood pressure at different sites, such as intracranial blood pressure in the head and neck. The blood pressure variation may facilitate much earlier discovery of an abnormality at a different position, such as artery vessel shape, vein vessel function and capillary blockage, which may greatly help to prevent any kind of fatal disease, such as potential hemorrhage in the head, etc.

Figure 4A:
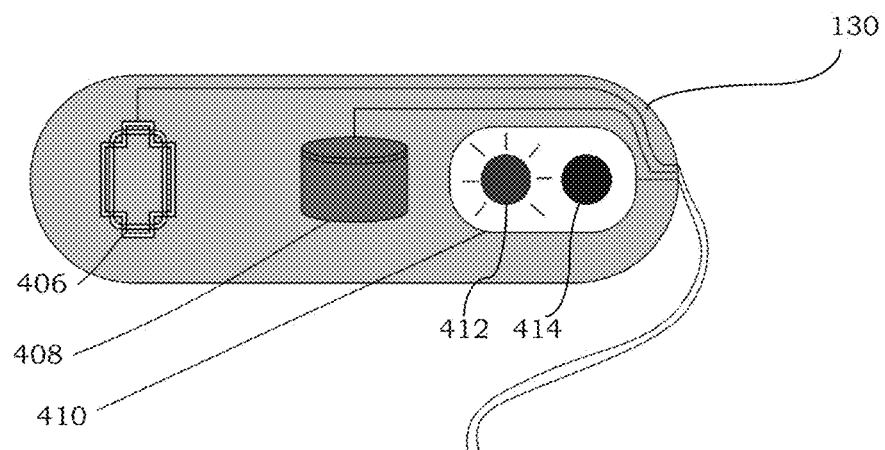
FIGS. 4a-b illustrate two exemplary kinds of non-invasive multi-channel sensor system.
Figure 4B:
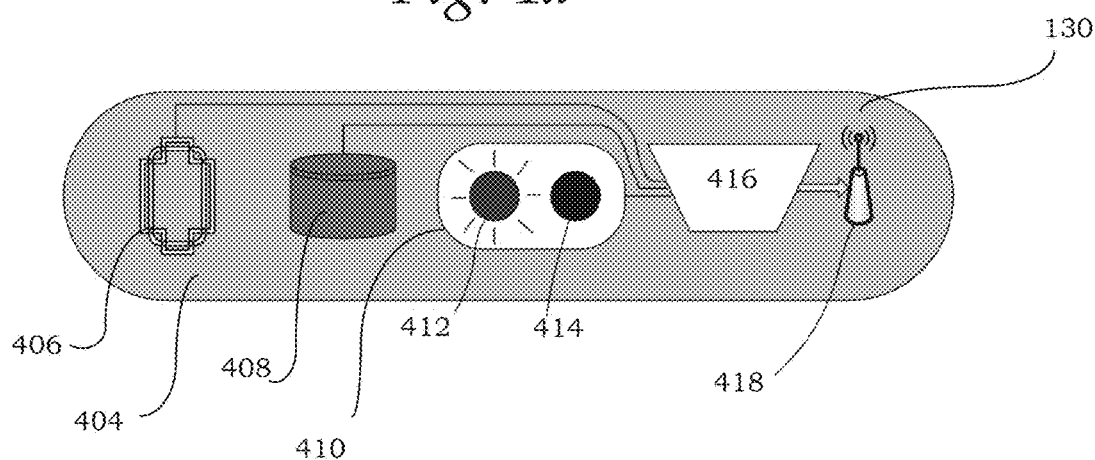

FIGS. 4a-b illustrate two exemplary kinds of non-invasive multi-channel sensor system 130. More particularly, FIG. 4a shows an exemplary wired version while FIG. 4b shows an exemplary wireless version of the multi-channel sensor system 130.

In the implementations shown, the multi-channel sensor system 130 includes three kinds of non-invasive sensors: blood flow sound sensor 406, blood pressure sensor 408 and laser light-based oximetric sensor 410. Such sensors may use ultrasound, laser vibration, oscillation, etc., to measure patient signals. It should be appreciated that other types of sensors may be used, and other types of patient signal data may be acquired. There may be some flexibility to add more sensors or install different kinds of sensors or transducers based on the particular clinical application and/or patient preference. For instance, a finger version, head version, chest version, etc. of the multi-channel sensor system 130 may be used. In some implementations, the blood flow sound sensor 406 is a vibration and/or oscillation sensing device that can convert mechanical signals produced by vibration and shaking to electrical analogue signals; the blood pressure sensor 408 is a force sensing device that can sense subtle changes for the muscle and skin force near the target blood vessel area; and the oximetric sensor 410 may use laser emitters 412 of different wavelengths and receiver 414 to calculate oxygen content and saturation levels. Although non-invasive sensors are shown, it should be appreciated that other different kinds of sensors, transducer systems or modules may also be installed. Additionally, sensor positions may be switchable within the housing of the system 130 to accommodate different locations on the patient's body. In this way, invasive and/or minimally invasive sensors for patient signal data acquisition and monitoring may be utilized.

Depending on the situation and clinical application (e.g., hospital versus portable system, ambulance, etc.), the wired version (as shown in FIG. 4a) or the wireless version (as shown in FIG. 4b) of the multi-channel sensor system 130 may be used. In the wireless version shown in FIG. 4b, an analog-to-digital conversion module 416 is provided to convert analog patient signals received from the sensors (406, 408 and 410) to digital signals. The digital signals may then be wirelessly communicated using, for example, a battery-powered wireless data transmission module 418 to computer system 101 for analysis.

Figure 5:
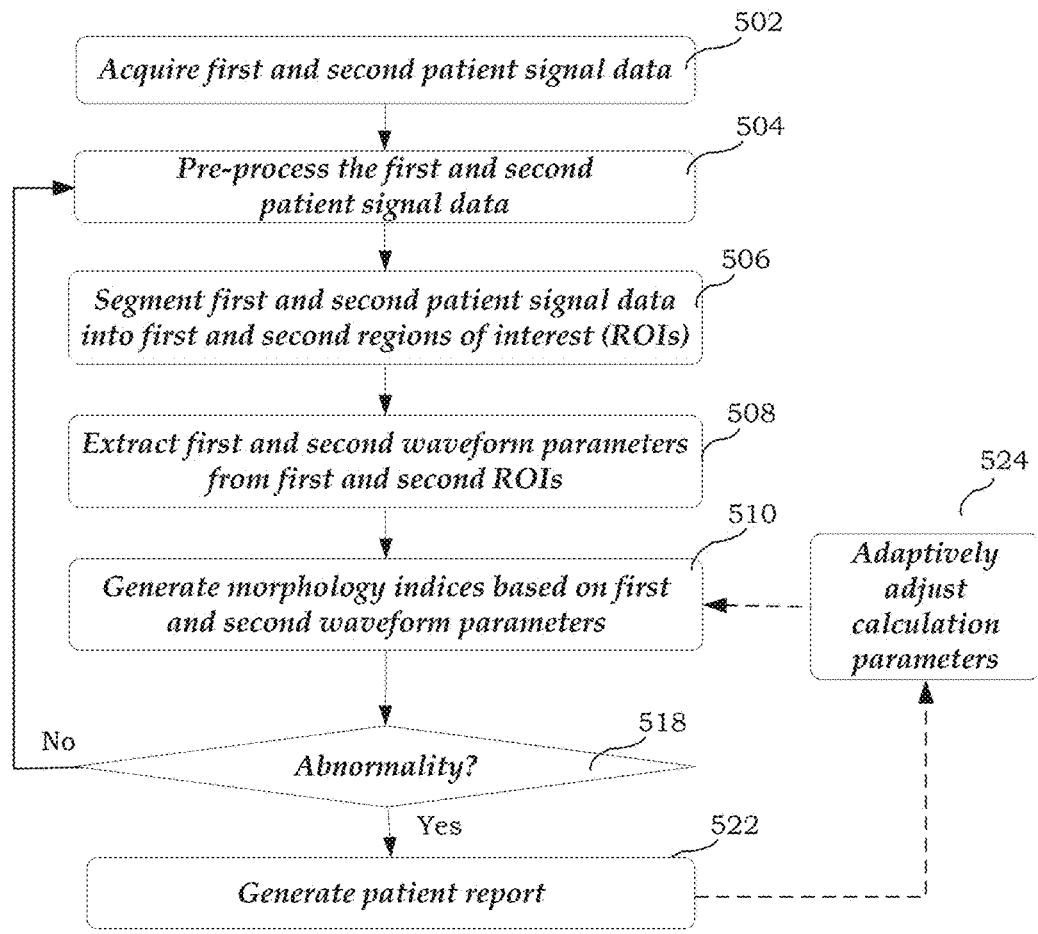
FIG. 5 shows an exemplary method of analyzing patient signals.

FIG. 5 shows an exemplary method 500 of analyzing patient signals. The method 500 may be applied for real-time monitoring, diagnosis and treatment of abnormalities (e.g., vessel pathology or a cardiac medical condition). The steps of the method 500 may be performed in the order shown or a different order. Additional, different, or fewer steps may be provided. Further, the method 500 may be implemented with the system 100 of FIG. 1, a different system, or a combination thereof.

At 502, patient monitor 130 acquires first and second patient signal data from a current patient. The first and second patient signal data may be acquired over multiple successive cycles. The first and second patient signal data may include digitized data of two different electrophysiological signals. For example, the first patient signal data may include blood pressure data while the second patient signal data may include oximetric (or SPO2) data. Alternatively, the first patient signal data may include blood flow sound data while the second patient signal data may include oximetric (or SPO2) data. Three or more different types of patient signal data may also be acquired. Alternatively, or additionally, other types of electrophysiological signal data, such as hemodynamic (HEMO), respiration (or capnographic), ECG or ICEG cardiac, and/or other vital sign signal data, other measurable patient biometric, physiological or medical signals, may also be acquired. In addition, other patient information, such as demographic data, clinical application and patient status, including, but not limited to, weight, height, gender, age, allergies, medications, etc., may also be acquired.

At 504, patient signal analysis unit 122 pre-processes the first and second patient signal data. Patient signal analysis unit 122 may pre-process the first and second patient signal data by filtering, amplification, digitization and/or buffering. For example, the patient signal data may be pre-filtered and amplified for display on, for instance, patient monitor 130. The patient signal data may be filtered to remove unwanted patient movement and respiratory artifacts, as well as power line noise. The filter may be adaptively selected in response to data indicating clinical application (e.g., ischemia detection application, rhythm analysis application). In some implementations, the patient signal data may be amplified, buffered, filtered and/or digitized to produce a continuous stream of digitized samples.

At 506, patient signal analysis unit 122 segments the first and second patient signal data into respective first and second regions of interest (ROI). Such segmentation may be performed continuously and in real-time. In some implementations, an ROI is a graphical deflection commonly observed on a typical electrophysiological signal waveform. The first and second ROIs may occur simultaneously during a common time window. One or more types of ROIs may be identified from the first and second patient signal data. Examples of ROI types include, but are not limited to, a blood pressure waveform cycle, a blood flow waveform cycle, a SPO2 waveform cycle, etc. A blood pressure and a blood flow cycle correspond to a cardiac cycle, since such cycles are determined by the heart. To segment the waveform, a peak and/or valley detector may be provided in the patient signal analysis unit 122 for detecting the start and end points of an ROI. The segmentation may be tailored to clinical needs and/or input from the user (e.g., doctor), which may help to more efficiently extract patient information.

Patient signal analysis unit 122 may determine the baseline value from the digitized patient signal data. The baseline value (or level) generally refers to a known threshold value with which an unknown (e.g., amplitude) is compared when measured or assessed. The baseline value may comprise a zero voltage line if a static (DC) voltage signal component is filtered out from the signal. For example, the baseline value may be a zero blood pressure level or a zero oxygen level. The baseline value may be automatically, semi-automatically or manually selected by the user. It may be selected and adaptively adjusted according to the current application and clinical requirements.

At 508, patient signal analysis unit 122 extracts first and second waveform parameters from the respective first and second ROIs. Such waveform parameters serve to describe the shape or morphology of the respective ROI. Such waveform parameters may include, for example, an amplitude data series. For instance, the amplitude of the patient signal in the first and second ROIs may be sampled at predetermined time intervals to generate respective first and second digitized amplitude data series. As another example, amplitudes of blood pressure, blood flow sound and oximetric signal waveforms may be sampled at key points to generate three different sets of amplitude data series. The waveform parameters may also include time points at key amplitude points, such as maximum amplitude, minimum amplitude, local amplitude turning points, and so forth. Other types of waveform parameters, such as the maximum amplitude, the minimum amplitude, or the end time point of diastolic signal amplitude, may also be extracted.

At 510, patient signal analysis unit 122 generates one or more morphology indices based on the first and second waveform parameters. Such morphology indices may serve to quantitatively compare the shapes of the first and second ROI waveforms extracted from the different patient signal data, so as to detect changes due to cardiac blood flow functionality or vessel abnormality, such as rigidity (vessel contracting-perfusion losing flexibility) of the vessel wall. Morphology indices may include, but are not limited to, morphology distribution ratios, mutual entropy values, unilateral ratios, bilateral ratios, or a combination thereof.

Figure 6:
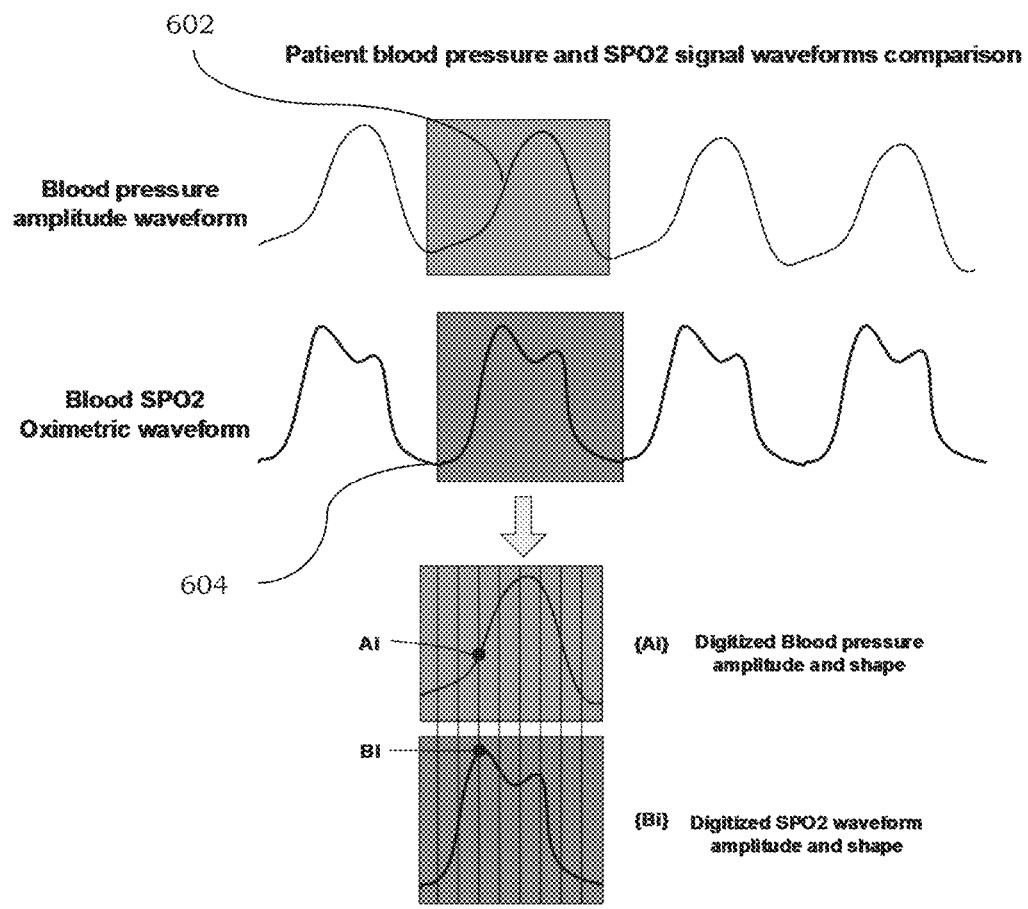
FIG. 6 illustrates the characterization and comparison of blood pressure and oximetric waveform shapes.

In some implementations, patient signal analysis unit 122 generates a morphology distribution ratio that compares blood pressure and oximetric signal data. FIG. 6 illustrates the characterization and comparison of blood pressure and oximetric (e.g., SPO2) waveform shapes. More particularly, a blood pressure signal waveform 602 and SPO2 oximetric signal waveform 604 are shown. The blood pressure and oximetric signal data may be acquired at the same location of the patient's body, such as arm, forehead, finger, etc. Both signal data may be categorized by heart cycle and signal amplitude.

Two sets of digitized signal amplitude data series {Ai} and {Bi} may be generated for the two signal waveforms (602 and 604) of the same cardiac or blood flow cycle. Ai and Bi are signal amplitude values of the two signals sampled during the corresponding time window. The user may define the resolution of the calculation according to calculation capacity and complexity. Based on the data sampling rate and resolution for the calculation, the size N of the digitized data series of one blood flow cycle ({Ai} or {Bi}) may be determined.

The morphology distribution ratio can be defined in one of the following exemplary forms:

$$\text{Morphology-distribution ratio} = \frac{\sum_{i=0 \text{ to } (N-1)} Ai}{\sum_{i=0 \text{ to } (N-1)} Bi} \quad (1)$$

$$\text{or Morphology-distribution ratio} = \sum_{i=0 \text{ to } (N-1)} \frac{Ai}{Bi} \quad (2)$$

$$\text{or Morphology-distribution ratio} = \sum_{i=0 \text{ to } (N-1)} \left|\frac{Ai}{Bi}\right| \quad (3)$$

wherein Ai and Bi are the amplitude values for corresponding data points at two selected regions of interest; i is an index from 0 to (N-1); and N is the total number of Ai or Bi amplitude values. The morphology-distribution ratio compares the shapes of blood pressure waveform 602 and oximetric waveform 604.

In some implementations, patient signal analysis unit 122 generates a mutual entropy value based on the first and second waveform parameters. The mutual entropy value is a cross signal information entropy value that further captures changes and distortions in patient signals (e.g., blood pressure and oximetric signals) caused by blood flow functionality. More particularly, the mutual entropy values describes the information energy changes between the patient signal waveforms, especially the statistical probability changes in the signal amplitude and cross information distribution.

In some implementations, the mutual entropy value of the blood pressure signal vs. oximetric signals can be defined as follows:

$$\text{Mutual-entropy} = -\sum_{i \in \Theta} p(i) \cdot \log(p(i)) \quad (4)$$

$$\text{wherein } p(i) = \frac{|Ai - Bi|}{\sum_{i \in \Theta} |Ai - Bi|} \quad (5)$$

wherein p(i) denotes the cross mutual probability; Ai and Bi are the first and second amplitude data series of the blood pressure signal waveform 602 and oximetric signal waveform 604; $\Theta$ is the cross mutual probability set that includes all signal comparison probabilities for each timing stamp.

In some implementations, patient signal analysis unit 122 generates unilateral and bilateral ratios between the patient signal data based on the first and second waveform parameters. Unilateral and bilateral ratios facilitate comparison of waveform parameters (e.g., time durations, energy contents, etc.) associated with patient signal data in two different ROIs. A unilateral ratio describes the signal ratio between the same or similar blood flow function portions of the two patient signals, while bilateral ratio describes the signal ratio between different blood flow function portions of the two patient signals.

Figure 7:
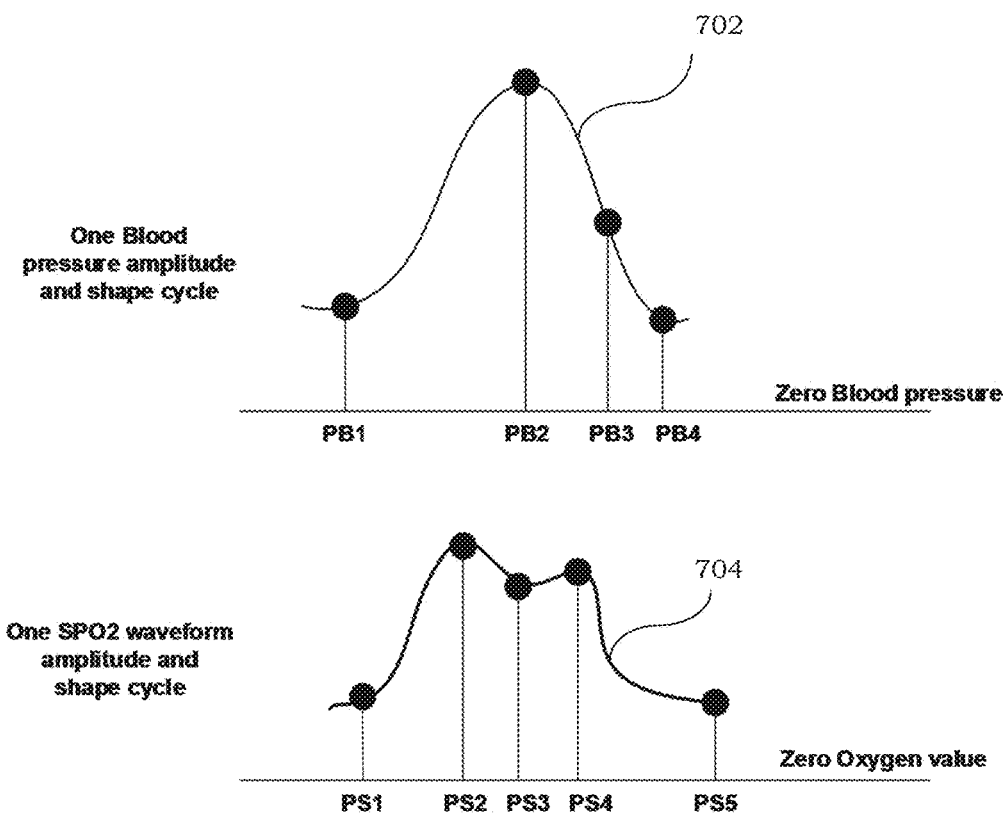
FIG. 7 illustrates an exemplary signal segmentation and categorization.

FIG. 7 illustrates an exemplary signal segmentation and categorization which may be utilized for blood pressure signal and SPO2 signal waveforms. Same (or similar) and different portions may be segmented from same blood flow or blood pressure cycle (or ROI) of the two patient signals. As shown, the segmentation may use various key amplitude points, such as maximum amplitude, minimum amplitude, and local amplitude turning points. It should be appreciated that other key points or segmentation methods may also be used, depending on different clinical applications and medical usages. Based on this signal segmentation, different parameters and indices may be defined for detecting and characterizing signal changes and blood flow functionality distortions.

Referring to FIG. 7, the blood pressure waveform 702 may be segmented into 3 functional portions by a set of 4 time points: PB1, PB2, PB3 and PB4, while the SPO2 oximetric cycle signal waveform 704 may be segmented into 4 functional portions by a set of 5 time points: PS1, PS2, PS3, PS4 and PS5. According to blood flow functionality, these different portions represent different stages of the blood flow timing and duration. The area in each portion represent energy content of the blood flow. Accordingly, two segmented portions from different patient signals may be compared to provide effective diagnosis and characterization of blood flow and vessel circulation information. In some implementations, the first and second patient signal data are blood pressure and SPO2 signal data. However, other different signal data, such as respiration, blood flow sound, ECG, ICEG, heart sound, muscle contracting force signals, etc., may also be compared.

In some implementations, unilateral and bilateral mutual time duration ratios are determined. Such time duration ratios may be determined as follows:

$$\text{Unilateral Time duration ratio}(UT) = \left|\frac{T_{PBi} - T_{PBj}}{T_{PSi} - T_{PSj}}\right| \quad (6)$$

$$\text{Bilateral Mutual Time duration ratio}(BMT) = \left|\frac{T_{PBi} - T_{PBj}}{T_{PSm} - T_{PSn}}\right| \quad (7)$$

wherein $T_{PBi}$ and $T_{PBj}$, are the time points of selected key amplitude points in the ROI of the blood pressure signal data and $T_{PSi}$, $T_{PSj}$, $T_{PSm}$ and $T_{PSn}$ are the time points of selected key amplitude points in the ROI of the oximetric signal data. These time duration ratios describe variations in the blood flow functional portions. For example, if the vessel wall is rigid, the blood pressure of the corresponding functional point is higher (although the functional duration of the blood pressure may not change), but the blood flow speed may slow down. The slower blood flow speed postpones or prolongs the SPO2 signal waveform. Accordingly, there may be changes in the ratio due to the prolonging of the SPO2 functional portion.

In some implementations, unilateral and bilateral mutual time duration averaging ratios are determined, as follows:

$$\text{Unilateral Time duration averaging ratio}(UTA) = \left|\frac{\text{mean}_N(T_{PBi} - T_{PBj})}{\text{mean}_N(T_{PSi} - T_{PSj})}\right| \quad (8)$$

$$\text{Bilateral Mutual Time duration averaging ratio}(BMTA) = \quad (9)$$

$$\left|\frac{\text{mean}_N(T_{PBi} - T_{PBj})}{\text{mean}_N(T_{PSm} - T_{PSn})}\right|$$

wherein N is the number of blood flow cycles that are used to calculate the average values of the time durations; mean denotes the averaging operation for N cycles, $T_{PBi}$ and $T_{PBj}$, are the time points of selected key amplitude points in the ROI of the blood pressure signal data and $T_{PSi}$, $T_{PSj}$, $T_{PSm}$ and $T_{PSn}$ are the time points of selected key amplitude points in the ROI of the oximetric signal data.

In some implementations, unilateral and bilateral mutual time duration variability ratios are determined, as follows:

$$\text{Unilateral Time duration variability ratio}(UTV) = \quad (10)$$

$$\left|\frac{\text{Variability}_N(T_{PBi} - T_{PBj})}{\text{Variability}_N(T_{PSi} - T_{PSj})}\right|$$

$$\text{Bilateral Mutual Time duration variabilit ratio}(BMTV) = \quad (11)$$

$$\left|\frac{\text{Variability}_N(T_{PBi} - T_{PBj})}{\text{Variability}_N(T_{PSm} - T_{PSn})}\right|$$

$$\text{Variability} = \left.\frac{\text{Mean}(\Delta T)}{\delta(\Delta T)}\right|_N \quad (12)$$

wherein Mean($\Delta T$) is the average value of the time duration $\Delta T$ and $\delta(\Delta T)$ is the standard deviation of the time duration $\Delta T$; N is the number of blood flow cycles which are used to calculate the average value of the time durations, $T_{PBi}$ and $T_{PBj}$, are the time points of selected key amplitude points in the ROI of the blood pressure signal data and $T_{PSi}$, $T_{PSj}$, $T_{PSm}$ and $T_{PSn}$ are the time points of selected key amplitude points in the ROI of the oximetric signal data.

In some implementations, unilateral and bilateral mutual energy duration ratios are determined, as follows:

$$\text{Unilateral energy duration ratio}(UE) = \left| \frac{E(PBi, PBj)}{E(PSi, PSj)} \right| \quad (13)$$

$$\text{Bilateral Mutual energy duration ratio}(BME) = \left| \frac{E(PBi, PBj)}{E(PSm, PSn)} \right| \quad (14)$$

$$E(T1, T2) = \int_{t \in [T1, T2]} |A(t)|^2 \quad (15)$$

wherein $E(T1, T2)$ denotes the energy value from timing T1 to timing T2; PBi and PBj, are time points of selected key amplitude points in the ROI of the blood pressure signal data used in calculating the energy duration, PSi, PSj, PSm and PSn are time points of selected key amplitude points in the ROI of the oximetric signal data used in calculating the energy duration, and $A(t)$ is the signal amplitude of the signal waveform within the ROI duration area and portion. Here, the unilateral energy duration ratio compares the energy between similar blood flow function portions of the blood pressure and SPO2 waveforms, while the bilateral mutual energy duration ratio compares the energy between any two functional portions of the blood pressure and SPO2 waveforms.

In some implementations, unilateral and bilateral mutual energy averaging ratios are determined, as follows:

$$\text{Unilateral energy duration averaging ratio}(UEA) = \quad (16)$$

$$\left| \frac{\underset{M}{\text{mean}}(E(PBi, PBj))}{\underset{M}{\text{mean}}(E(PSi, PSj))} \right|$$

$$\text{Bilateral Mutual energy duration averaging ratio}(BMEA) = \quad (17)$$

$$\left| \frac{\underset{M}{\text{mean}}(E(PBi, PBj))}{\underset{M}{\text{mean}}(E(PSm, PSn))} \right|$$

wherein $$\underset{M}{\text{mean}}(\bullet)$$

is the average value for M blood flow cycles (typically, blood flow cycles are generated at the same rate as cardiac cycles).

In some implementations, unilateral and bilateral mutual energy variability ratios are determined, as follows:

$$\text{Unilateral energy duration variability ratio}(UEV) = \quad (18)$$

$$\left| \frac{\underset{M}{\text{Variability}}(E(PBi, PBj))}{\underset{M}{\text{Variability}}(E(PSi, PSj))} \right|$$

-continued $$\text{Bilateral Mutual energy duration variability ratio}(BMEV) = \quad (19)$$

$$\left| \frac{\underset{M}{\text{Variability}}(E(PBi, PBj))}{\underset{M}{\text{Variability}}(E(PSm, PSn))} \right|$$

$$\text{Variability} = \left. \frac{\text{Mean}(\text{Energy}(\text{ROI\_portion}))}{\delta(\text{Energy}(\text{ROI\_portion}))} \right|_M \quad (20)$$

wherein PBi and PBj, are time points of selected key amplitude points in the ROI of the blood pressure signal data used in calculating the energy duration, PSi, PSj, PSm and PSn are time points of selected key amplitude points in the ROI of the oximetric signal data used in calculating the energy duration, Mean(Energy($\bullet$)) is the average energy value of the ROI signal portion; $\delta(\Delta T)$ is the standard deviation value of the ROI signal portion; and M is the number of blood flow cycles used to calculate the average values of the time durations.

In some implementations, patient signal analysis unit 122 generates cross mutual time delay parameters. In some implementations, a ROI mutual time delay is generated as follows:

$$\text{Mutual Time Delay (MTD)} = \text{Time duration(PBx, PSy)} \quad (21)$$

wherein Time duration (time1, time2) shows the time delay between Time Point 1 corresponding to a blood pressure waveform point and Time Point 2 corresponding to a SPO2 oximetric waveform point; PBx and PSy are time points in blood pressure and SPO2 signal data.

In some implementations, a cross mutual time delay ratio is generated as follows:

$$\text{Cross Mutual Time Delay Ratio 1} = \frac{MTD(PBx, PSy)}{T_{Blood\ Flow\ Cycle\ length}} \quad (22)$$

$$\text{Cross Mutual Time Delay Ratio 2} = \frac{MTD(PBx, PSy)}{MTD(PBm, PSn)} \quad (23)$$

wherein $T_{Blood\ Flow\ Cycle\ length}$ is the time duration of the blood flow cycle which can be derived from the cardiac cycle length, such as the RR duration in a surface ECG signal; and MTD(PBx, PSy) is the time duration or delay between PBx in the blood pressure signal waveform and PSy in the SPO2 signal waveform. Cross Mutual Time Delay Ratio 1 is the ratio of an ROI time delay to the whole blood flow cycle, while Cross Mutual Time Delay Ratio 2 is the ratio of two ROI time delays of the selected time duration in blood pressure and SPO2 signal waveforms.

In some implementations, a ROI cross mutual time delay variability is generated as follows:

$$ROI\ \text{Cross Mutual Time Delay variability} = \quad (24)$$

$$\left. \frac{\text{Mean}(MTD(PBx, PSy))}{\delta(MTD(PBx, PSy))} \right|_M$$

wherein PBx and PSy are time points in blood pressure and SPO2 signal data, Mean($\bullet$) and $\delta(\bullet)$ are the average value and standard deviation of the cross mutual time delay with a calculation shift window of size M (i.e., M cycles of blood flow procedure are employed in the calculation). The ROI cross mutual time delay variability reflects changes in time durations, particularly those associated with blood flow functionality changes in the heart and vessels.

Returning to FIG. 5, at 518, patient signal analysis unit 122 determines, based at least in part on one or more of the generated morphology indices, whether the patient has an abnormality. Based on the clinical application and patient status, clinical users may decide and select which generated morphology index should be used. The abnormality may be, for example, vessel pathology or a cardiac medical condition, such as cardiac arrhythmia, cardiac tissue and electrophysiological-hemodynamic malfunctions, etc. The abnormality may be identified based on, for instance, threshold values.

In some implementations, different types of generated morphology indices, associated statistical parameters and/or other input patient data (e.g., demographic data, other hemodynamic, electrophysiological and vital signs data, etc.) are linearly or non-linearly combined to generate patient health status, abnormality type, severity or location, treatment suggestions, and/or other types of output. Different methods, such as an artificial neural network (ANN), fuzzy algorithm, etc., may be used to integrate the input patient data.

Figure 8:
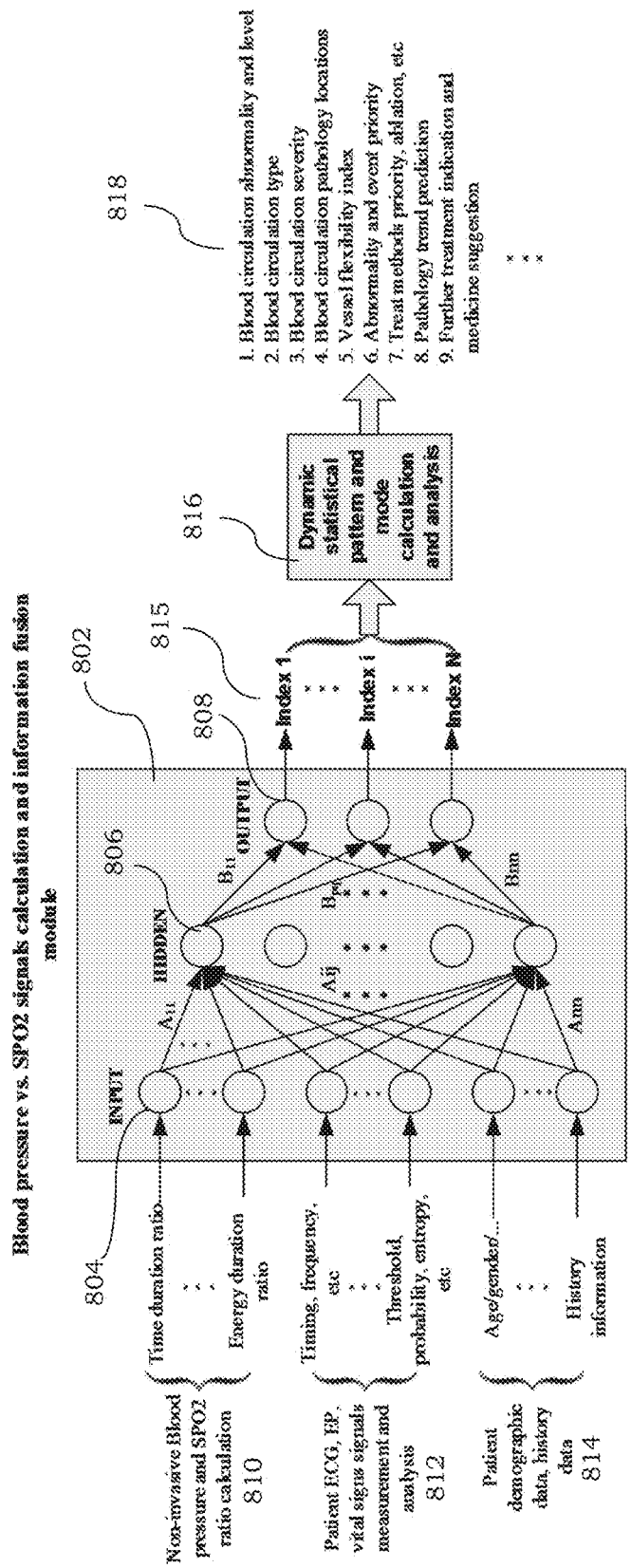
FIG. 8 shows an exemplary artificial neural network (ANN) structure.

FIG. 8 shows an exemplary ANN structure 802 for integrating multiple types of patient data for providing cardiac function analysis and decision support in diagnosis and treatment of blood circulation pathologies. Exemplary ANN structure 802 includes three layers—input layer 804, hidden layer 806 and output layer 808—for combining and integrating different kinds of determined blood pressure and SPO2 ratios and/or associated parameters 810, other patient signal data (e.g., ECG, EP, HEMO and other vital sign signal data) 812 and patient status, demographic data, clinical application and other information (e.g., age, gender, medical history, weight, height, medication, allergies, etc.) 814. ANN structure 802 combines and maps patient data 810, 812 and 814 to indices (1 to i to N) 815. The indices 815 may correspond to data results that may be mapped to output parameters 818.

Statistical module 816 performs dynamic statistical pattern analysis on the indices 815 to generate output parameters 818 that provide a more detailed characterization of cardiac circulation information for users (e.g., patients, doctors, etc.). Exemplary statistical pattern analysis include, for example, T test, student test, or any hypothesis testing for validating the results. Output parameters 818 may indicate, for example, vessel flexibility level, blood circulation abnormality, type, severity, pathology locations, vessel flexibility index, abnormality and event priority, treatment priorities, ablation parameters, future pathology trend prediction, suggestions for further treatment and medication, and so forth. Such output parameters 818 may be used for the detection, diagnosis, warning, evaluation and/or treatment of abnormalities. They may be used in different clinical applications, such as in operating room (OR) monitoring, critical monitoring in an intensive care unit (ICU), critical care unit (CCU) or emergency room (ER), patient status and health monitoring, etc. The output parameters may also be used to control and adaptively adjust treatment devices or systems. For example, a closed-loop implantable cardioverter-defibrillator (ICD) system based on blood pressure to SPO2 signal ratio calculation and diagnosis may be built for an automatic treatment and drug delivery system.

$A_{ij}$ are weights applied between the input layer 804 and hidden layer 806, while $B_{pq}$ are weights applied between the hidden layer 806 and output layer 808 of the ANN computation. $A_{ij}$ weights and $B_{pq}$ weights are adaptively adjusted and tuned using a training data set. ANN unit 802 may incorporate a self-learning function that processes new input data 810, 812 and 814 to increase the precision and accuracy of calculated results. The exemplary ANN-based hemodynamic blood pressure and SPO2 signal diagnosis may combine ratios and parameters generated by the framework described herein, with information derived from a medical professional's experience (input and suggested controlling mode) to provide more quantitative and qualitative results and evaluation of patient health status (e.g., determination of vessel flexibility, cardiac blood flow functionality, etc.). The generated signal ratios 810 and data fusion indices 815 may be used in any kind of patient and clinical environment.

If an abnormality is not identified, the method 500 may return to step 504. If an abnormality is identified, the method 500 may proceed to step 522. At 522, patient signal analysis unit 122 generates a patient report. The patient report may indicate the abnormality, associated characteristics (e.g., location, type, severity, timing, etc.) and other information (e.g., suggested treatment options). The patient report may be in the form of, for example, an alert message presented at patient monitor 130. The patient report may be stored in database 124 for future retrieval.

At 524, patient signal analysis unit 122 may optionally adaptively adjust calculation parameters used for calculating the afore-mentioned ratios and parameters. The adaptive adjustment may be performed automatically, semi-automatically or manually by the clinical user. Such calculation parameters include, but are not limited to, number of samples in a calculation window, time steps, thresholds, and so forth.

The present framework may be used for any kind of blood circulation abnormality detection and characterization, especially for cardiac functionality characterization and vessel diagnosis. A computer simulation was performed to demonstrate blood pressure to SPO2 signal ratio analysis for blood vessel flexibility characterization.

Figure 9:
FIG. 9 shows a table that compares results generated for two episodes of patient signals.

FIG. 9 shows a table 902 that compares results generated for two episodes of patient signals: normal artery and a low flexibility artery. The blood pressure and SPO2 signals are acquired from the arm position (see FIG. 3). For comparison with traditional patient signal data measurement, results from three methods were measured and calculated: (1) normal blood pressure measurement (systolic pressure vs. diastolic pressure), (2) normal SPO2 saturation reading from an optical oximetric sensor, and (3) bilateral mutual time duration variability (BMTV). The BMTV was calculated using 5 blood flow cycles, a time duration for blood pressure waveform from PB1 to PB3, and a time duration for SPO2 waveform from PS1 to PS4.

The results from the blood pressure measurement and SPO2 oxygen saturation data calculation do not show any difference between the normal arm artery and the low flexibility arm artery (especially with the Senior population). However, the BMTV shows a significant difference: for the normal artery, the bilateral mutual time duration variability ratio is 2.8, while the BMTV drastically increases to 13.6 for the low flexibility arm artery. The blood flow is changing due to the artery wall losing flexibility, which may result in delay and waveform changes in the SPO2 signal. In this specific example, the higher the BMTV, the less flexible the arm artery. The BMTV may have better sensitivity and provide new results for doctor and clinical application, such as blood flow system and circulation monitoring and verification. Based on the different blood pressure vs. SPO2 ratios and monitoring locations, the threshold and severity level may be different for flexibility and pathology function evaluation and characterization. This preliminary work may provide some evidence and proof for the framework described herein. The present framework may also be utilized for cardiac functionality diagnosis and ICD treatment. Especially with multi-channel combined sensing and monitoring system, the abnormality and pathology of the vessel system and cardiac functions may be more accurately diagnosed, such as type, location, severity, etc.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A computer-implemented method of patient signal analysis, comprising:
   receiving over multiple successive cycles, from a patient monitor including a first sensor and a second sensor, a first and a second patient signal data, wherein the first patient signal data is a characterization of one of blood flow information and vessel circulation information and the second patient signal data is a characterization of one of blood flow information and vessel circulation information that is different from the first patient signal data characterization;
   pre-processing the first and the second patient signal data by a patient signal analysis unit;
   segmenting, by a processor, the pre-processed first and the second patient signal data into respective first and second regions of interest;
   extracting, by the processor, a respective first and a respective second waveform parameters from the first and the second regions of interest; and
   generating, by the processor, one or more respective morphology indices based on the respective first and the respective second waveform parameters over the multiple successive cycles;
   comparing, by the processor, shapes of the one or more respective morphology indices to detect at least one of a change due to cardiac blood flow functionality and vessel abnormality;
   determining, by the processor, whether an abnormality exists in at least one of the first and the second patient signal data based on the results of the comparison of the one or more respective morphology indices; and
   if an abnormality is determined, generating, by the patient signal analysis unit, a patient report alert on the multi-channel patient monitor.

2. The method of claim 1 wherein the first and the second waveform parameters comprise a first and a second amplitude data series.

3. The method of claim 2 wherein the one or more morphology indices are generated based on the first and the second amplitude data series.

4. The method of claim 2 wherein the one or more morphology indices comprise one or more mutual entropy values.

5. The method of claim 1 wherein the first and the second waveform parameters comprise a first and a second set of time points associated with key amplitude points.

6. The method of claim 5 wherein the key amplitude points include at least one maximum amplitude, at least one minimum amplitude and at least one local amplitude turning point.

7. The method of claim 5 wherein the one or more morphology indices comprise one or more unilateral or bilateral time duration ratios.

8. The method of claim 5 wherein the one or more morphology indices comprise one or more unilateral or bilateral time duration averaging ratios.

9. The method of claim 5 wherein the one or more morphology indices comprise one or more unilateral or bilateral time duration variability ratios.

10. The method of claim 5 wherein the one or more morphology indices comprise one or more unilateral or bilateral energy duration ratios.

11. The method of claim 5 wherein the one or more morphology indices comprise one or more unilateral or bilateral energy duration averaging ratios.

12. The method of claim 5 wherein the one or more morphology indices comprise one or more unilateral or bilateral energy variability ratios.

13. The method of claim 5 wherein the one or more morphology indices comprise one or more cross mutual time delays.

14. The method of claim 5 wherein the one or more morphology indices comprise one or more cross mutual time delay ratios.

15. The method of claim 5 wherein the one or more morphology indices comprise one or more cross mutual time delay variabilities.

16. The method of claim 1 further comprising non-linearly combining, via an artificial neural network structure, the one or more morphology indices with input patient data.

17. The method of claim 1, the blood flow information and the vessel circulation information each being one of respiration, blood flow sound, electrocardiography, intra-cardiac electro-gram, heart sound, and muscle contracting force signals.

18. The method of claim 1, the one or more morphology indices being one of morphology distribution ratios, mutual entropy values, unilateral ratios, bilateral ratios, and a combination thereof.

19. The method of claim 1, the patent report alert including a patient health status report resulting from combining one or more of the respective morphology indices with at least one of associated statistical parameters, demographic data, hemodynamic data, electrophysiological data, and vital sign data.

* * * * *